(12) United States Patent
Blackburn et al.

(10) Patent No.: US 8,535,391 B2
(45) Date of Patent: Sep. 17, 2013

(54) CATALYSED DYE SYSTEMS

(75) Inventors: Richard Simon Blackburn, Leeds (GB); Patrick Columba McGowan, Leeds (GB); Christopher Martin Pask, Leeds (GB); Christopher Mark Rayner, Leeds (GB)

(73) Assignee: University of Leeds, Leeds, Yorkshire (GB)

( * ) Notice: Subject to any disclaimer, the term of this patent is extended or adjusted under 35 U.S.C. 154(b) by 0 days.

(21) Appl. No.: 13/381,126

(22) PCT Filed: Jun. 30, 2010

(86) PCT No.: PCT/EP2010/059322
§ 371 (c)(1),
(2), (4) Date: Dec. 28, 2011

(87) PCT Pub. No.: WO2011/000892
PCT Pub. Date: Jan. 6, 2011

(65) Prior Publication Data
US 2012/0110751 A1    May 10, 2012

(30) Foreign Application Priority Data
Jul. 2, 2009  (GB) .................................. 0911493.5

(51) Int. Cl.
*A61Q 5/10*    (2006.01)
(52) U.S. Cl.
USPC ................ 8/405; 8/406; 8/408; 8/410; 8/411; 8/435; 8/621; 8/628; 8/629

(58) Field of Classification Search
USPC ............. 8/405, 406, 408, 410, 411, 421, 435, 8/621, 628, 629
See application file for complete search history.

(56) References Cited

U.S. PATENT DOCUMENTS

| 5,993,491 A | 11/1999 | Lim et al. |
| 6,648,925 B1 * | 11/2003 | Mayer et al. ...................... 8/405 |
| 2004/0148712 A1 | 8/2004 | Pruche et al. |
| 2008/0233068 A1 | 9/2008 | Forbes et al. |

FOREIGN PATENT DOCUMENTS

| DE | 19852972 A1 | 5/2000 |
| EP | 0342034 A2 | 11/1989 |
| EP | 1891927 A2 | 2/2008 |

* cited by examiner

*Primary Examiner* — Eisa Elhilo
(74) *Attorney, Agent, or Firm* — Ward and Smith, P.A.

(57) ABSTRACT

The present invention is concerned with a dye system for application to a substrate, the dye system comprising: (a) at least one dye precursor; (b) an oxidizing agent; and (c) a catalyst, wherein the catalyst is a homogeneous catalyst or a heterogeneous catalyst. Preferably, the catalyst comprises at least one metal-containing compound. The invention also envisages a method for the coloration of a substrate, the method comprising treating the substrate with the dye system of the invention. In preferred embodiments of the invention, the substrate comprises human hair, natural or synthetic polymers, or textile fibers. In further preferred embodiments, the at least one dye precursor is an organic precursor, the at least one metal derivative for use as a catalyst comprises at least one inorganic metal compound or at least one metal complex comprising at least one organic ligand, and the oxidizing agent is hydrogen peroxide.

18 Claims, 3 Drawing Sheets

CATALYSED DYE SYSTEMS

FIELD OF THE INVENTION

This invention relates to multi-component catalysed dye systems which are particularly applicable to the dyeing of textile fibres and, most especially, human hair. Most particularly, it is concerned with oxidative dye systems.

BACKGROUND TO THE INVENTION

The dyeing of textile fibres is a major industry throughout the world and efforts are continually being made to find new and improved materials for this purpose which can provide improvements in terms of factors such as economy, dyeing properties, health and safety and environmental considerations. There is particular interest in developing dyes which can be conveniently and efficiently applied to textile fibres, and which provide intense shades having good fastness properties at reasonable cost.

Coloration of hair, from a social perspective, is a major business, with the numbers of people colouring their hair, both in professional salons and in the home, steadily increasing (http://www.pg.com; http://www.henkel.com). However, people applying colorants to their hair and having their hair coloured are exposed to significant health risks in view of the nature of the materials in use, and it is desirable that alternative natural, non-toxic, non-carcinogenic means of hair coloration are developed in order to minimise any potential hazards to human health. In addition, currently available hair colorants are derived from non-sustainable sources, consuming fossil fuels in their production, and it would be desirable if natural plant-based dyes could instead be utilised in the hair coloration industry.

Permanent hair coloration currently represents at least 80% of the hair coloration market (J. S. Anderson, *J. Soc. Dyers Col.*, 2000, 116, 193). This system relies on the diffusion of uncoloured precursors into the hair where they undergo oxidation reactions to produce the desired colour in situ; these colorants usually last at least 24 shampoos. Permanent oxidative hair coloration typically involves three components, as follows:

(a) the primary intermediate (or "base"), which is usually an ortho- or para-substituted (hydroxy, amine, substituted amine) aromatic amine (e.g. 1-5);

(b) the coupler, which is generally an aromatic compound with at least one (usually two meta-) electron donating group (e.g. 6-13); and

(c) an oxidant, which is almost always hydrogen peroxide ($H_2O_2$).

1

2

3

4

5

6

7

8

9

10

-continued

However, significant concerns exist with regard to the potential toxicological effects of the components which are used, particularly aromatic amines which represent nearly all of the primary intermediates employed, as many of these are suspect carcinogens, tumorgens or mutagens, and may effect reproduction (http://hazard.com/msds/tox). Indeed, it is believed that many of the primary intermediates and couplers may be banned for human use within the foreseeable future. In 2008, the World Health Organisation announced evidence that the hair dye component p-phenylenediamine (PPD; 1) increases the risk of bladder cancer (Cancer Research UK, http://www.cancerhelp.org.uk/help/default.asp?page=4124); PPD is an important component of most hair colorant formulations and, whilst alone it is a suspected carcinogen, in the presence of hydrogen peroxide and the absence of couplers, it may form a trimer—"Bandrowski's base", as shown in Scheme 1 and discussed by M. Picardo, C. Cannistraci, A. Cristaudo, C. de Luca and B. Santucci (*Dermatologica*, 1990, 181, 104)—which is known to be mutagenic (B. N. Ames, H. O. Kammen and E. Yamasaki, *Proc. Natl. Acad. Sci. USA*, 1975, 72, 2423).

SCHEME 1
FORMATION OF BANDROWSKI'S BASE BY OXIDATION
OF P-PHENYLENEDIAMINE

PPD and other compounds, such as p-toluenediamine (PTD; 2), resorcinol (6) and ammonia can also provoke severe adverse reactions when used in hair and skin coloration (C. J. Le Coz, C. Lefebvre, F. Keller, E. Grosshans, *Arch. Dermatol.* 2000, 136, 1515; C. J. Le Coz, Rev. Fr. *Aller. Immunol. Clin.* 2001, 41, 504, M. Onder, C. A. Atahan, P. Oztas, M. O. Oztas, *Int. J. Dermatol.* 2001, 40, 577). Allergic contact dermatitis is commonly associated with exposure to p-phenylenediamine, as noted by E. M. Coulter, C. Jenkinson, Y. Wu, J. Farrell, B. Foster, A. Smith, C. McGuire, C. Pease, D. Basketter, C. King, P. S. Friedmann, M. Pirmohamed, B. K. Park and D. J. Naisbett, (*J. Investig. Dermatol.* 2008, 128, 897). Such suspect compounds are used in most hair colorant formulations and are essential for brown and black shades, which are the most popular colours. Hence, it is desirable, and potentially necessary, to use colorants that pose no significant health hazard; this would necessarily involve a combination of less hazardous synthetic components and greater use of natural compounds.

In addition, many oxidative hair coloration systems rely on the use of alkaline agents, typically ammonia, in order to raise the hair cuticle, thereby allowing the dye precursors to penetrate the hair more easily, whilst also activating hydrogen peroxide. Clearly, improved systems which eliminated the requirement for the use of ammonia would also be desirable.

WO-A-2006/106366 discloses an oxidative hair dye system which eliminates the use of p-phenylenediamine, and which comprises a hair dye, a supposed organometallic compound and an oxidising agent. The supposed organometallic compound is stated to be preferably an organotitanate compound, particularly a tetraalkyl titanate or a titanate chelate. Such compounds are stated to be useful for enhancing the substantivity of topical compositions applied to the body, these compositions comprising one or more cosmetic and/or therapeutic benefit agents, a bonding agent having hydrolysable or exchangeable ligands, and a carrier.

The present inventors have investigated the use of a broader range of metal-containing catalysts in hair dyeing systems in order to avoid the use of potentially harmful materials. The inventors have found that suitable systems may be based on combinations of organic precursors with metal-containing catalysts and oxidising agents. Many of these dye systems also find application in dyeing textile fibre substrates.

SUMMARY OF THE INVENTION

Thus, according to a first aspect of the present invention, there is provided a dye system for application to a substrate, said dye system comprising:
 (a) at least one dye precursor;
 (b) an oxidising agent; and
 (c) a catalyst,
wherein said catalyst is a homogeneous catalyst or a heterogeneous catalyst.

In preferred embodiments of the invention, said catalyst comprises at least one metal-containing compound.

In one preferred embodiment of the invention, said substrate comprises human hair. In alternative embodiments of the invention, said substrate comprises a natural or synthetic polymeric substrate. Additional embodiments of the invention envisage the use of textile fibre substrates.

In one preferred embodiment of the invention, said at least one dye precursor is an organic precursor. Said embodiment is especially preferred when said dye system is intended for application to human hair.

Typically, said at least one dye precursor comprises an aromatic amino compound, a phenolic compound, or an aminophenolic compound.

In another preferred embodiment of the invention, said at least one metal-containing compound for use as a catalyst comprises at least one inorganic metal compound.

In an alternative embodiment of the invention, said at least one metal-containing compound for use as a catalyst comprises at least one metal complex comprising at least one organic ligand.

Typical oxidising agents, especially for the dyeing of textile substrates, include percarbonates, persulphates, organic peracids and organic hydroperoxides. In certain circumstances, molecular oxygen (including air) may also be used. A preferred oxidising agent, however, is hydrogen peroxide.

According to a second aspect of the present invention, there is provided a method for the coloration of a substrate, said method comprising:
(a) treating said substrate with at least one dye precursor;
(b) treating said substrate with an oxidising agent; and
(c) treating said substrate with a catalyst,
wherein said catalyst is a homogeneous catalyst or a heterogeneous catalyst.

In the most preferred embodiments of the second aspect of the invention, said catalyst comprises at least one metal-containing compound.

In a preferred embodiment of the second aspect of the invention, said treatments of said substrate with at least one dye precursor, an oxidising agent and a catalyst are carried out simultaneously. In an alternative embodiment of the invention, said treatments are carried out sequentially.

Preferably, said method is performed by treating said substrate in aqueous solutions comprising said dye systems.

In preferred embodiments of the invention, said substrate is selected from human hair, natural or synthetic polymeric substrates, or textile fibre substrates. When said substrate comprises human hair, it is preferred that said method is carried out at ambient temperatures. In the case of natural or synthetic polymeric substrates and textile fibres, said method may be carried out at any suitable temperature and pressure. Thus, in certain embodiments, textile fibre coloration is carried out at atmospheric pressure and at a temperature which is preferably in the range from 20°-110° C. In alternative embodiments, textile fibre coloration may take place at elevated pressures. Pressures anywhere in the range of 1-500 bar may be employed but, typically, suitable pressures would be in the range of 1-20 bar, with corresponding elevated temperatures in the range from 100°-200° C. being employed, as appropriate.

In preferred embodiments of the method according to the second aspect of the invention, at least one of the following conditions applies:
said at least one dye precursor comprises an organic precursor, which is preferably an oxidisable organic precursor and may, for example, be selected from an aromatic amino compound, a phenolic compound or an aminophenolic compound;
said at least one metal-containing compound for use as a catalyst comprises at least one inorganic metal compound or at least one metal complex comprising at least one organic ligand; and
said oxidising agent is hydrogen peroxide.

DESCRIPTION OF THE INVENTION

In the most preferred embodiments, the dye systems of the invention are applied to human hair.

Preferred examples of said at least one dye precursor comprise existing hair dye components such as p-aminophenol (4), o-aminophenol (5), p-amino-o-cresol (8), m-aminophenol (9), p-chlororesorcinol (10), 2,3-dihydroxynaphthalene (11) and 3-methylcatechol (12), similarly functionalised precursors not currently used as hair dye components, such as 4-methylresorcinol (14), p-aminobenzoic acid (15) which also finds application as a UV filter in some sunscreens, 1,3-dihydroxynaphthalene (16) and 1,4-dihydroxynaphthalene (17), in addition to naturally occurring compounds and derivatives thereof, examples of which include phenolic compounds such as gallic acid (18), tannic acid (19), vanillin (20), phloroglucinol (21) and orcinol (22), and derivatives thereof.

These materials may all be applied as components of dye systems according to the first aspect of the invention, in combination with an oxidising agent and a catalyst, by a method according to the second aspect of the invention. Thus, in certain embodiments each of these derivatives was individually tested as a hair dye precursor in a system comprising at least one metal-containing catalyst and an oxidising agent, usually in the form of hydrogen peroxide, and each was applied to bleached white hair swatches. The use of m-aminophenol and p-amino-o-cresol resulted in dark red/brown shades, o-aminophenol yielded a brown shade, and p-aminophenol produced an almost black coloration. In addition, p-chlororesorcinol and 2,3-dihydroxynaphthalene both gave a blonde colour, whilst the use of 3-methylcatechol resulted in a medium brown shade. Gallic acid and tannic acid, both of which are polyphenols found in certain woods and tea leaves, both resulted in significant red/brown coloration. Phloroglucinol, which may be isolated from the bark of fruit trees, orcinol, which is present in many species of lichen, and catechol—found in fruit and vegetables such as apples and potatoes—all produce a blonde colour, whilst vanillin produced a blonde colour naturally smelling of vanilla, which offered a potentially useful additional feature.

Suitable derivatives of these naturally occurring phenolic compounds include derivatives of salicylic acid, such as 5-aminosalicylic acid (23), whilst aromatic amino derivatives such as isatin (24), 1-methylindole (25) and 2-methylindole (26) also find application according to the invention:

When applied to bleached white hair swatches in combination with a catalyst and an oxidising agent, 5-aminosalicylic acid produced a light brown colour, whilst isatin and 2-methylindole both resulted in a pale yellow colour and 1-methylindole produced a green colour.

In further preferred embodiments of the invention, said at least one metal-containing compound for use as a catalyst comprises at least one inorganic metal compound. Preferred inorganic metal compounds comprise compounds of d-block transition metals such as scandium, titanium, vanadium, chromium, molybdenum, iron, manganese, cobalt, nickel, copper, zirconium and zinc including, but not limited to, the acetates, acetylacetonates, aluminates, bicarbonates, borates, bromates, carbonates, chlorites, cyanides, diethylcitrates, halides, hexafluoroacetylacetonates, hexafluorophosphates, hexafluorosilicates, dihydrogen phosphates, hydrogen carbonates, hydrogen sulphates, hydrogen sulphides, hydrogen sulphites, hydroxides, hypochlorites, iodates, nitrates, nitrites, oxalates, oxides, perfluorophthalocyanines, peroxides, phosphates, phthalocyanines, pyrophosphates, silicates, sulphamates, sulphates, sulphides, sulphites, tartrates, tetrafluoroborates, thiocyanates, thiolates, thiosulphates, tosylates and triflates of these metals.

Especially preferred compounds in this context include $TiBr_2$, $TiBr_4$, $TiCl_2$, $TiCl_3$, $TiCl_4$, $TiF_3$, $TiF_4$, $Ti_2O_3$, $TiO(SO_4)$, $(TiO_2)(SiO_2)$, $TiS_2$, $VBr_3$, $VCl_2$, $VCl_3$, $VCl_4$, $V_2O_3$, $V_2O_4$, $V_2O_5$, $VO(SO_4)$, $VOCl_3$, $VOF_3$, $V(C_5H_7O_2)_3$, $VO(C_5H_7O_2)_2$, $VO(OR)_3$, $Mo_2(OCOCH_3)_4$, $Mo(CO)_6$, $MoCl_3$, $MoCl_5$, $MoO_2Cl_2$, $MoF_6$, $MoO_2$, $MoO_3$, $MoS_2$, $MoOCl_4$, $MoSO_4$, $Mn(OCOCH_3)_2$, $Mn(OCOCH_3)_2.xH_2O$, $Mn(C_5H_7O_2)_2$, $MnBr_2$, $MnBr_2.xH_2O$, $MnCO_3$, $MnCO_3.xH_2O$, $Mn_2(CO)_{10}$, $MnCl_2$, $MnCl_2.xH_2O$, $MnF_2$, $MnF_3$, $Mn(HCO_2)_2.xH_2O$, $MnI_2$, $Mn(NO_3)_2$, $Mn(NO_3)_2.xH_2O$, $Mn_3O_4$, $Mn_2O_3$, $MnO_2$, $Mn(C_{32}H_{16}N_8)$, $MnSO_4$, $MnSO_4.xH_2O$, $MnS$, $Fe(OCOCH_3)_2$, $Fe(OCOCH_3)_3$, $FeBr_2$, $FeBr_3$, $FeCl_2$, $FeCl_2.xH_2O$, $FeCl_3$, $FeCl_3.xH_2O$, $Fe(OEt)_3$, $FeSO_4.NH_3CH_2CH_2NH_3SO_4.4H_2O$, $Fe_4[Fe(CN)_6]_3$, $FeF_2$, $FeF_3$, $FeF_3.xH_2O$, $FeI_2$, $Fe(CH_3CHOHCOO)_2.xH_2O$, $Fe(NO_3)_3.xH_2O$, $Fe(C_2O_4).xH_2O$, $FeO$, $Fe_2O_3$, $Fe_3O_4$, $FePO_4.xH_2O$, $Fe(C_{32}H_{16}N_8)$, $FeSO_4.xH_2O$, $FeS$, $Fe(BF_4).xH_2O$, $FeO_3Ti$, $Fe(SCN)_2$, $Co(OCOCH_3)_2$, $Co(OCOCH_3)_2.xH_2O$, $Co(C_5H_7O_2)_2$, $Co(C_5H_7O_2)_2.xH_2O$, $Al_2CoO_4$, $CoBr_2$, $CoBr_2.xH_2O$, $CoCO_3$, $CoCO_3.xH_2O$, $Co_2(CO)_8$, $CoCl_2$, $CoCl_2.xH_2O$, $CoF_2$, $Co[CH_3(CH_2)_3CH(C_2H_5)CO_2]_2$, $Co(OH)_2$, $CoI_2$, $Co(NO_3)_2$, $Co(NO_3)_2.xH_2O$, $Co(O_2O_4)$, $Co(C_2O_4).xH_2O$, $CoSO_4$, $CoSO_4.xH_2O$, $Co(BF_4)_2$, $Co(BF_4)_2.xH_2O$, $Co(SCN)_2$, $Ni(OCOCH_3)_2$, $Ni(OCOCH_3).xH_2O$, $Ni(C_5H_7O_2)_2$, $NiBr_2$, $NiBr_2.xH_2O$, $NiCO_3$, $Ni(CO_3).xNi(OH)_2$, $NiCl_2$, $NiCl_2.xH_2O$, $NiOCoO$, $Ni[CH_3(CH_2)_3CH(C_2H_5)CO_2]_2$, $NiF_2$, $Ni(OH)_2$, $NiI_2$, $Ni(NO_3)_2$, $Ni(NO_3)_2.xH_2O$, $Ni(C_2O_4)$, $Ni(C_2O_4).xH_2O$, $NiO_2$, $NiO_2.xH_2O$, $Ni(C_{32}H_{16}N_8)$, $Ni(SO_3NH_2)_2$, $Ni(SO_3NH_2)_2.xH_2O$, $NiSO_4$, $NiSO_4.xH_2O$, $Ni_3S_2$, $NiZnFe_4O_4$, $CuOCOCH_3$, $Cu(OCOCH_3)_2$, $Cu(OCOCH_3)_2.xH_2O$, $Cu(C_5H_7O_2)_2$, $CuBr$, $CuBr_2$, $CuCO_3$, $CuCO_3.Cu(OH)_2$, $CuCl$, $CuCl_2$, $CuCl_2.xH_2O$, $Cu[CH_3(CH_2)_3CH(C_2H_5)CO_2]_2$, $CuF_2$, $CuF_2.xH_2O$, $Cu(HCO_2)_2$, $Cu(HCO_2)_2.xH_2O$, $Cu(OH)_2$, $Cu_2(OH)PO_4$, $CuI$, $CuFe_2O_4$, $Cu(NO_3)_2$, $Cu(NO_3)_2.xH_2O$, $Cu_2O$, $CuO$, $Cu(C_{32}H_{16}N_8)$, $Cu_2P_2O_7.xH_2O$, $CuSO_4$, $CuSO_4.xH_2O$, $CuS$, $Cu[O_2CCH(OH)CH(OH)CO_2].xH_2O$, $Cu(BF_4)_2$, $Cu(BF_4).xH_2O$, $Cu(SCN)$, $Zn(OCOCH_3)_2$, $Zn(OCOCH_3)_2.xH_2O$, $Zn(C_5H_7O_2)_2$, $Zn(C_5H_7O_2)_2.xH_2O$, $ZnBr_2$, $ZnBr_2.xH_2O$, $ZnCl_2$, $ZnF_2$, $Zn(C_{32}F_{16}N_8)$, $Zn(C_5HF_6O_2)_2$, $Zn(C_5HF_6O_2)_2.xH_2O$, $ZnSiF_6.xH_2O$, $ZnI_2$, $ZnFe_2O_4$, $Zn(NO_3)_2$, $Zn(NO_3)_2.xH_2O$, $Zn(C_2O_4)$, $Zn(C_2O_4).xH_2O$, $ZnO$, $ZnO.xH_2O$, $ZnO_2$, $Zn_3(PO_4)_2$, $Zn(C_{32}H_{16}N_8)$, $ZnSO_4$, $ZnSO_4.xH_2O$, $ZnS$, $Zn(BF_4)2$, $Zn(BF_4)_2.xH_2O$, $Zn_2TiO_4$, $Zr(OCOCH_3)_4$, $Zr(OCOCH_3)_x(OH)_{4-x}$, $Zr(C_5H_7O_2)_4$, $Zr(C_{26}H_{44}O_{16})$, $ZrCO_3(OH_2)_2.ZrO_2$, $ZrCl_4$, $ZrF_4$, $ZrF_4.xH_2O$, $Zr(HPO_4)_2$, $Zr(OH)_4$, $ZrI_4$, $ZrO(NO_3)_2$, $ZrO(NO_3)_2.xH_2O$, $Zr(SO_4)_2$, $Zr(SO_4)_2.xH_2O$, $ZrOCl_2$ and $ZrOCl_2.xH_2O$. These compounds may, for example, be applied in combination with readily available aminophenolic compounds, such as p- or m-aminophenol, and oxidising agents such as hydrogen peroxide.

Thus, when applied in combination with p-aminophenol and hydrogen peroxide, the Fe compounds produced dark brown colours whilst $ZnCl_2$ and $ZnF_2$ provided very intense red brown colours, and $ZrCl_2O$ and $MnCl_2$ provided very dark brown, almost black colours. However, certain differences were observed when these materials were used in combination with m-aminophenol so that Fe compounds again give dark brown colours, as did $ZrCl_2O$ and $MnCl_2$, whilst $ZnCl_2$ and $ZnF_2$ gave no coloration at all. This difference in behaviour is considered to be due to the difference in ease of oxidation between the two organic species, with p-aminophenol undergoing oxidation far more readily than m-aminophenol.

Alternative metal compounds for use as catalysts comprise salts of the alkali metals of Group 1, such as potassium, or the alkaline earth metals of Group 2, for example magnesium. Specific examples of suitable salts include acetates, acetylacetonates, aluminates, bicarbonates, borates, bromates, carbonates, chlorites, cyanides, diethylcitrates, halides, hexafluoroacetylacetonates, hexafluorophosphates, hexafluorosilicates, dihydrogen phosphates, hydrogen carbonates, hydrogen sulphates, hydrogen sulphides, hydrogen sulphites, hydroxides, hypochlorites, iodates, nitrates, nitrites, oxalates, oxides, perfluorophthalocyanines, peroxides, phosphates, phthalocyanines, pyrophosphates, silicates, sulphamates, sulphates, sulphides, sulphites, tartrates, tetrafluoroborates, thiocyanates, thiolates, thiosulphates, tosylates and triflates, such as $KAl(SO_4)_2$ $K_2CO_3$, $K_3PO_4$, $KNO_3$, $KCl$, $MgSO_4$, $Mg_3(PO_4)_2$, $MgCO_3$, $Mg(NO_3)_2$ and $MgCl_2$.

When applied in combination with p-aminophenol and hydrogen peroxide, $MgSO_4$ produced a very intense red brown colour, whilst $KAl(SO_4)_2$ gave rise to a very dark brown, almost black colour. However, differences were again observed when these salts were used in combination with m-aminophenol wherein $KAl(SO_4)_2$ only yielded a pale brown colour, and $MgSO_4$ gave no coloration at all.

In certain embodiments of the invention wherein said at least one metal-containing compound comprises at least one inorganic metal compound, said catalyst comprises at least one mineral or clay. Preferred examples of said minerals or clays include anatase, brookite, eudialyte, ilmenite, perovskite, rutile, sabaite, titanite, zircon, zirconolite, zircohylite or zirkelite.

In preferred embodiments of the invention, said substrate is selected from human hair, natural or synthetic polymeric substrates, or textile fibre substrates. Preferably, said method is performed by treating said substrate in aqueous solutions comprising said dye systems. When said substrate comprises human hair, it is preferred that said method is carried out at ambient temperatures. In the case of natural or synthetic polymeric substrates, or textile fibres, said method may be carried out at any suitable temperature and pressure. Thus, in certain embodiments, textile fibre coloration is carried out at atmospheric pressure and at a temperature which is preferably in the range from 20°-110° C. In alternative embodiments, textile fibre coloration may take place at elevated pressures. Pressures anywhere in the range of 1-500 bar may be employed but, typically, suitable pressures would be in the range of 1-20 bar, with corresponding elevated temperatures in the range from 100°-200° C. being employed, as appropriate.

It is preferred that, when performing the method according to the second aspect of the invention for treating human hair, at least one of the following conditions applies:
  said at least one dye precursor comprises an organic precursor, which is preferably an oxidisable organic precursor and may, for example, be selected from the group of naturally occurring phenolic compounds previously disclosed herein, an aromatic amino compound, a phenolic compound or an aminophenolic compound;
  said at least one metal-containing compound for use as a catalyst comprises at least one inorganic metal compound, most preferably a compound of a d-block transition metals such as iron, manganese, zirconium and zinc, or a salt of an alkali metal of Group 1, such as potassium, or an alkaline earth metal of Group 2, for example magnesium; and
  said oxidising agent is hydrogen peroxide.

In alternative embodiments of the invention, the dye systems of the invention are applied to substrates which comprise textile fibres. Application of the dye systems according to the invention to textile fibres may be achieved by treating said fibres with the dye systems of the first aspect of the invention according to the method of the second aspect of the invention. Typically, application of dyes is achieved by treatment of a substrate with at least one dye precursor, an oxidising agent and a catalyst, wherein said catalyst comprises at least one metal-containing compound, by a method wherein said treatments are carried out simultaneously. Alternatively, however, said treatments may be carried out sequentially.

When applying said dye systems to textile fibres, it is preferred that said at least one metal-containing compound for use as a catalyst comprises at least one metal complex comprising at least one organic ligand. It is also preferred that said at least one dye precursor comprises an aromatic amino compound, a phenolic compound or an aminophenolic compound such as p- or m-aminophenol, and that said oxidising agent is hydrogen peroxide.

In the context of the present invention, particularly suitable catalysts which comprise at least one metal complex comprising at least one organic ligand are metal chelates, most particularly titanium complexes comprising at least one organic ligand. Typical ligands include optionally substituted alkyl ligands. A particularly preferred example of such a catalyst is titanium triethanolamine isopropyl chelate complex.

In certain embodiments of the invention wherein the dye systems of the invention are applied to substrates which comprise textile fibres, dye precursors comprising aromatic amino compounds, phenolic compounds and/or aminophenolic compounds may be employed. Thus, for example, excellent results have been achieved when utilising N,N-bis (hydroxyethyl)-p-phenylenediamine sulphate (27), and particularly suitable aminophenolic compounds include m-aminophenol (9) and p-amino-o-cresol (8).

27

Application of at least one of these dye precursors to textile fibre substrates in the presence of metal containing catalysts and hydrogen peroxide has been found to give promising results on textile substrates including wool, cotton, polypropylene, polyester, polyetherketone, p-aramid, m-aramid and lyocell. Particularly impressive results have been observed in the case of wool.

Thus, it has been observed that the use of m-aminophenol and N,N-bis(hydroxyethyl) -p-phenylenediamine sulphate as dye precursors with wool substrates leads to significant coloration at room temperature over a period of two hours, giving brown and yellow/green dyeings, respectively, whilst dyeings carried out on wool with p-aminophenol and m-aminophenol as precursors yielded brown colours, and red shades on wool were observed with a p-amino-o-cresol precursor.

However, when m-aminophenol and N,N-bis(hydroxyethyl)-p-phenylenediamine sulphate have been applied to wool in combination as dye precursors under reflux conditions, significantly more intense coloration has been observed, giving very dark brown shades.

The dye systems according to the invention have also been successfully applied to natural and synthetic polymeric substrates such as polyethylene, poly(vinyl chloride), rubber and leather, as well as to paper.

Application of the dyes of the first aspect of the invention according to the method of the second aspect of the invention is preferably carried out using the same basic procedure as for hair dyes, wherein the substrate is typically treated in an aqueous mixture containing the three components of the dyeing system. Most preferably said treatments are carried out simultaneously in a one-stage process. Alternatively, however, said treatments may be carried out sequentially via a two-stage process. Thus, in the one-stage dyeing process, the dye precursor, catalyst and hydrogen peroxide are applied at the same time, whilst in the two-stage process, the dye precursor is applied first, over a period of about 30 minutes, after which the catalyst and hydrogen peroxide are applied.

Said treatments may be carried out at any suitable temperature, but the preferred temperature range is from 20°-110° C. Preferred pH conditions for the dyeing of wool are in the range of 5-8.

Figure 1:
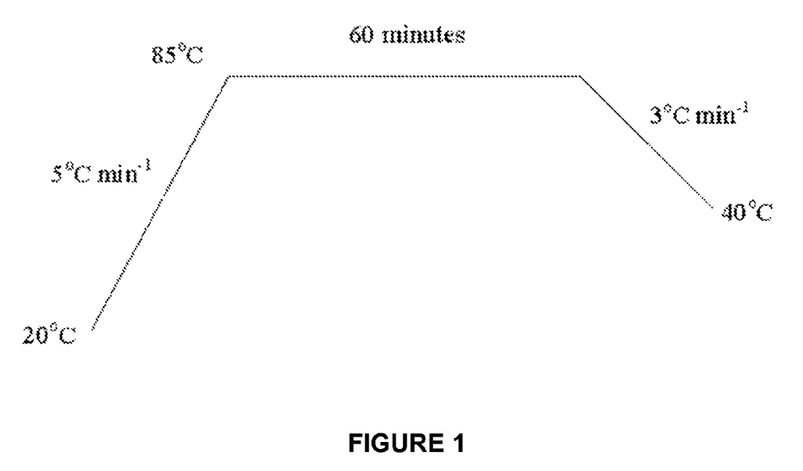
FIG. 1 is a dyeing profile for the dyeing of wool according to the method of the invention as described in Example 4.
Figure 2:
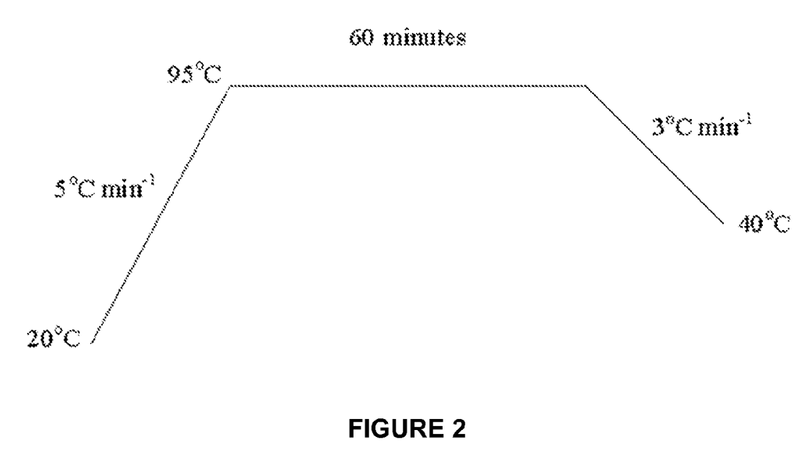
FIG. 2 is a dyeing profile for the dyeing of cotton according to the method of the invention as described in Example 5.
Figure 3:
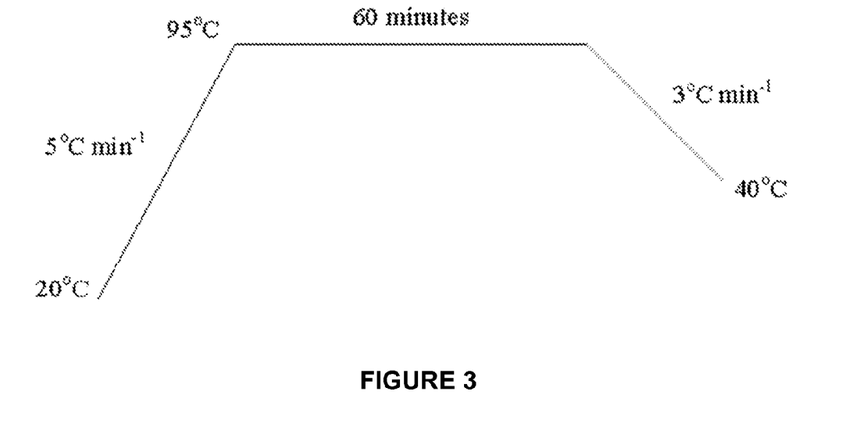
FIG. 3 is a dyeing profile for the dyeing of Lyocell according to the method of the invention as described in Example 6.
Figure 4:
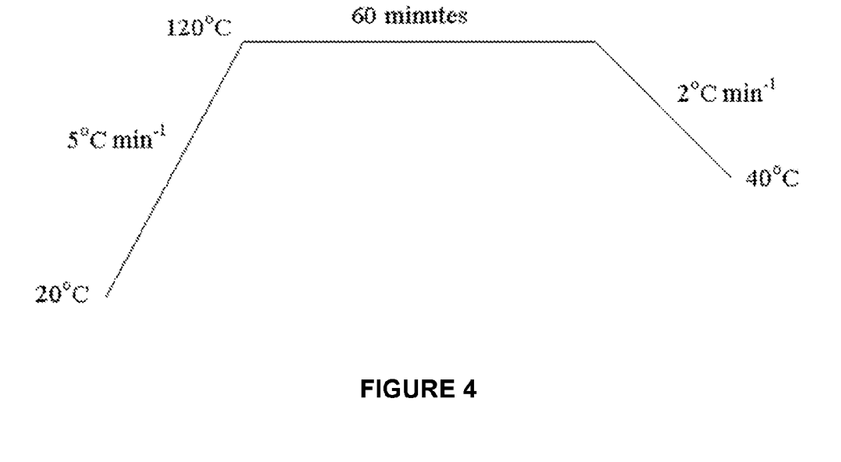
FIG. 4 is a dyeing profile for the dyeing of p-Aramidl according to the method of the invention as described in Example 7.
Figure 5:
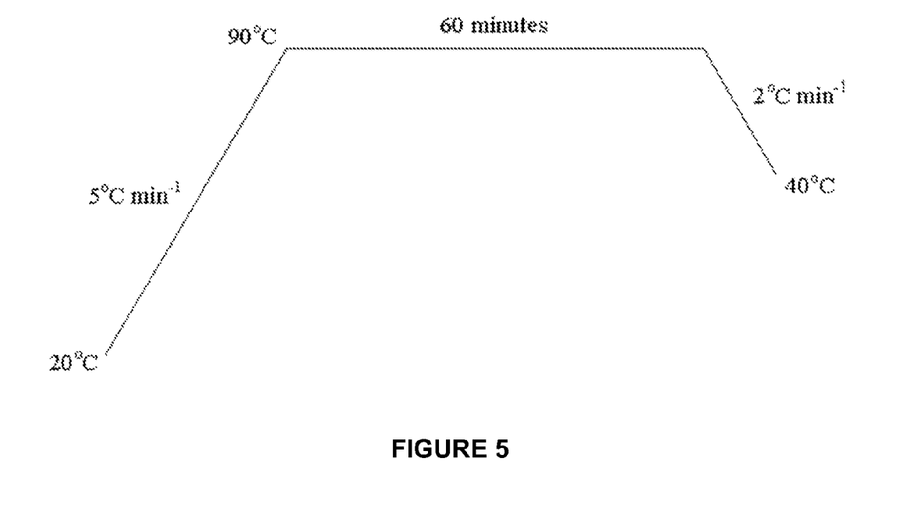
FIG. 5 is a dyeing profile for the dyeing of polypropylene according to the method of the invention as described in Example 8.
Figure 6:
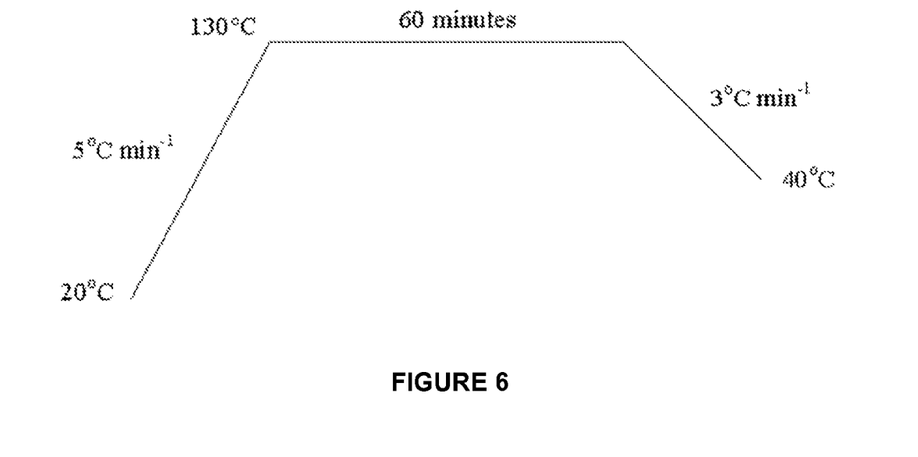
FIG. 6 is a dyeing profile for the dyeing of PET/cotton blend according to the method of the invention as described in Example 9.

The invention will now be further illustrated, though without in any way limiting its scope, by reference to the following Examples and the accompanying FIGS. 1-6.

EXAMPLES

Example 1

Dyeing of Hair

Solutions of dye precursor (100 mg) and $ZrOCl_2$ (100 mg) in water (20 ml) were prepared and added to glass jars. Into each jar was suspended a bleached blonde hair swatch. Hydrogen peroxide (0.1 ml) was added, the jars sealed, and the mixtures shaken for 60 minutes, after which the swatches were removed, rinsed in warm water and air dried. The results are summarised in Table 1.

TABLE 1

Colours observed when dyeing hair swatches with various dye precursors and $ZrOCl_2$ catalyst according to the invention

| Precursor | Colour |
| --- | --- |
| p-Aminophenol | Brown |
| o-Aminophenol | Brown |
| 1,4-Dihydroxynaphthalene | Orange/red |
| Isatin | Yellow |
| p-Phenylenediamine | Black |
| m-Aminophenol | Red/brown |
| 3-Methylcatechol | Brown |
| Catechol | Blonde |
| p-Amino-o-cresol | Orange/red |

Example 2

Dyeing of Hair

Solutions of m-aminophenol (30 mg) in water (10 ml) were prepared and added to glass jars. Catalyst (30 mg) was added, and a bleached blonde hair swatch suspended in each jar. Hydrogen peroxide (0.1 ml) was added, the jars sealed and the mixtures shaken for 60 minutes, after which the swatches were removed, rinsed in warm water and air dried. The results are summarised in Table 2.

TABLE 2

Colours observed when dyeing hair swatches using m-aminophenol dye precursor and various catalysts according to the invention

| Catalyst | Colour |
| --- | --- |
| BLANK | No colour |
| $VO(OiPr)_3$ | Brown |
| $VOSO_4$ | Brown |
| $MnO_2$ | Grey |
| $MnCl_2 \cdot xH_2O$ | Brown |
| $NH_4VO_3$ | Brown |
| $V_2O_5$ | Brown |
| AZG-370 (Aluminium Zirconium Tetrachlorohydrex Glycine Complex) | Brown |
| AZP-908 (Aluminium Zirconium Tetrachlorohydrex Glycine Complex) | Brown |

TABLE 2-continued

Colours observed when dyeing hair swatches using m-aminophenol dye precursor and various catalysts according to the invention

| Catalyst | Colour |
| --- | --- |
| REZAL 67 (Aluminium Zirconium Pentachlorohydrate Solution) | Brown |
| ZIRCALEM G36L (Aluminium Zirconium Tetrachlorohydrex Glycinate Solution) | Brown |

Example 3

Dyeing of Hair

Solutions of p-amino-o-cresol (30 mg) in water (10 ml) were prepared and added to glass jars. Catalyst (30 mg) was added, and a bleached blonde hair swatch suspended in each jar. Hydrogen peroxide (0.1 ml) was added, the jars sealed and the mixtures shaken for 60 minutes, after which the swatches were removed, rinsed in warm water and air dried. The results are summarised in Table 3.

TABLE 3

Colours observed when dyeing hair swatches using p-amino-o-cresol dye precursor and various catalysts according to the invention

| Catalyst | Colour |
| --- | --- |
| BLANK | No colour |
| VO(OiPr)$_3$ | Orange/brown |
| VOSO$_4$ | Orange/brown |
| MnO$_2$ | Brown |
| MnCl$_2$•xH$_2$O | Orange/brown |
| NH$_4$VO$_3$ | Orange/brown |
| V$_2$O$_5$ | Brown |
| AZG-370 (Aluminium Zirconium Tetrachlorohydrex Glycine Complex) | Orange |
| AZP-908 (Aluminium Zirconium Tetrachlorohydrex Glycine Complex) | Orange |
| REZAL 67 (Aluminium Zirconium Pentachlorohydrate Solution) | Orange |
| ZIRCALEM G36L (Aluminium Zirconium Tetrachlorohydrex Glycinate Solution) | Orange |

Example 4

Dyeing of Wool

Wool was first scoured using 2 g dm$^{-3}$ Sandozin NIN for 15 minutes at 60° C. The fabric was then dyed according to the following procedure:
1) Dye precursor (10% on weight of fibre) was added to the aqueous dyebath at a liquor ratio of 20:1 and mixed;
2) Fabric was wetted and added to the dyebath;
3) Titanium triethanolamine isopropyl chelate complex (10 ml dm$^{-3}$) was added to the dyebath and mixed;
4) Hydrogen peroxide (10 ml dm$^{-3}$) was added to the dyebath and mixed; and The results are summarised in Table 4. The dyeings were seen to produce union shades.

TABLE 4

Colours observed when dyeing wool using various dye precursors and titanium triethanolamine isopropyl chelate complex catalyst according to the invention

| Precursor | Colour |
| --- | --- |
| p-Phenylenediamine | Black |
| m-Aminophenol | Brown |
| p-Aminophenol | Brown |
| p-Amino-o-cresol | Brown |
| Purpurin | Pink |
| Curcumin | Orange |
| Metol | Brown |

Example 5

Dyeing of Cotton

Cotton fabric was dyed according to the following procedure:
1) Dye precursor (10% on weight of fibre) was added to the aqueous dyebath at a liquor ratio of 20:1 and mixed;
2) Fabric was wetted and added to the dyebath;
3) Titanium triethanolamine isopropyl chelate complex (10 ml dm$^{-3}$) was added to the dyebath and mixed;
4) Hydrogen peroxide (10 ml dm$^{-3}$) was added to the dyebath and mixed; and The results are summarised in Table 5. The dyeings were seen to produce union shades.

TABLE 5

Colours observed when dyeing cotton using various dye precursors and titanium triethanolamine isopropyl chelate complex catalyst according to the invention

| Precursor | Colour |
| --- | --- |
| p-Phenylenediamine | Brown |
| m-Aminophenol | Brown |
| p-Aminophenol | Brown |
| p-Amino-o-cresol | Brown |
| Purpurin | Purple |
| Curcumin | Orange |
| Metol | Brown |

Example 6

Dyeing of Lyocell

Lyocell was first scoured using 2 g dm$^{-3}$ Sandozin NIN and 1 g dm$^{-3}$ Na$_2$CO$_3$ for 15 min at 60° C. The fabric was then dyed according to the following procedure:
1) Dye precursor (10% on weight of fibre) was added to the aqueous dyebath at a liquor ratio of 20:1 and mixed;
2) Fabric was wetted and added to the dyebath;
3) Titanium triethanolamine isopropyl chelate complex (10 ml dm$^{-3}$) was added to the dyebath and mixed;
4) Hydrogen peroxide (10 ml dm$^{-3}$) was added to the dyebath and mixed;

The results are summarised in Table 6. The dyeings were seen to produce union shades.

TABLE 6

Colours observed when dyeing lyocell using various dye precursors and titanium triethanolamine isopropyl chelate complex catalyst according to the invention

| Precursor | Colour |
|---|---|
| p-Phenylenediamine | Brown |
| m-Aminophenol | Brown |
| p-Aminophenol | Brown |
| p-Amino-o-cresol | Brown |
| Purpurin | Purple |
| Curcumin | Orange |
| Metol | Brown |

Example 7

Dyeing of p-Aramid p-Aramid fibre was dyed according to the following procedure:

1) Dye precursor (10% on weight of fibre) was added to the aqueous dyebath at a liquor ratio of 20:1 and mixed;
2) Fabric was wetted and added to the dyebath;
3) Titanium triethanolamine isopropyl chelate complex (10 ml dm$^{-3}$) was added to the dyebath and mixed;
4) Hydrogen peroxide (10 ml dm$^{-3}$) was added to the dyebath and mixed;

The results are summarised in Table 7. The dyeings were seen to produce union shades.

TABLE 7

Colours observed when dyeing p-aramid using various dye precursors and titanium triethanolamine isopropyl chelate complex catalyst according to the invention

| Precursor | Colour |
|---|---|
| p-Phenylenediamine | Brown |
| m-Aminophenol | Brown |
| p-Aminophenol | Brown |
| p-Amino-o-cresol | Brown |
| Purpurin | Pink |
| Curcumin | Orange |
| Metol | Brown |

Example 8

Dyeing of Polypropylene

The polymer was dyed according to the following procedure:

1) Dye precursor (10% on weight of fibre) was added to the aqueous dyebath at a liquor ratio of 20:1 and mixed;
2) Fabric was wetted and added to the dyebath;
3) Titanium triethanolamine isopropyl chelate complex (10 ml dm$^{-3}$) was added to the dyebath and mixed;
4) Hydrogen peroxide (10 ml dm$^{-3}$) was added to the dyebath and mixed; and The results are summarised in the Table 8. The dyeings were seen to produce union shades.

TABLE 8

Colours observed when dyeing polypropylene using various dye precursors and titanium triethanolamine isopropyl chelate complex catalyst according to the invention

| Precursor | Colour |
|---|---|
| p-Phenylenediamine | Brown |
| m-Aminophenol | Brown |
| p-Aminophenol | Brown |
| p-Amino-o-cresol | Brown |
| Purpurin | Purple |
| Curcumin | Orange |

Example 9

Dyeing of PET/Cotton Blend

The fabric was dyed according to the following procedure:

1) Dye precursor (10% on weight of fibre) was added to the aqueous dyebath at a liquor ratio of 20:1 and mixed;
2) Fabric was wetted and added to the dyebath;
3) Titanium triethanolamine isopropyl chelate complex (10 ml dm$^{-3}$) was added to the dyebath and mixed;
4) Hydrogen peroxide (10 ml dm$^{-3}$) was added to the dyebath and mixed;

The results are summarised in Table 9. The dyeings were seen to produce union shades.

TABLE 9

Colours observed when dyeing PET/cotton blend using various dye precursors and titanium triethanolamine isopropyl chelate complex catalyst according to the invention

| Precursor | Colour |
|---|---|
| p-Phenylenediamine | Brown |
| m-Aminophenol | Brown |
| p-Aminophenol | Brown |
| p-Amino-o-cresol | Brown |
| Purpurin | Purple |
| Curcumin | Orange |
| Metol | Brown |

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A dye system for application to a substrate, said dye system comprising:
   (a) at least one dye precursor;
   (b) an oxidising agent; and
   (c) a catalyst,
wherein said catalyst is a homogeneous catalyst or a heterogeneous catalyst;
and further wherein said catalyst comprises a mineral or clay, which optionally comprises at least one of anatase, brookite, eudialyte, ilmenite, perovskite, rutile, sabaite, titanite, zircon, zirconolite, zircohylite or zirkelite.

2. The dye system of claim 1, wherein said substrate is selected from the group consisting of human hair, a natural or synthetic polymeric substrate, and a textile fiber substrate.

3. The dye system of claim 1, wherein said catalyst comprises at least one metal-containing compound, and said at least one metal-containing compound for use as a catalyst optionally comprises at least one inorganic metal compound, which is optionally selected from the group consisting of at least one compound of a d-block transition metal, the salts of the alkali metals of Group 1, and the alkaline earth metals of Group 2.

4. The dye system of claim 3, wherein said d-block transition metal is selected from the group consisting of scandium, titanium, vanadium, chromium, molybdenum, iron, manganese, cobalt, nickel, copper, zirconium and zinc, or said alkali metal of Group 1 comprises potassium, or said alkaline earth metal of Group 2 comprises magnesium.

5. The dye system of claim 3, wherein said at least one inorganic metal compound is selected from the group consisting of an acetate, acetylacetonate, aluminate, bicarbonate, borate, bromate, carbonate, chlorite, cyanide, diethylcitrate, halide, hexafluoroacetylacetonate, hexafluorophosphate, hexafluorosilicate, dihydrogen phosphate, hydrogen carbonate, hydrogen sulphate, hydrogen sulphide, hydrogen sulphite, hydroxide, hypochlorite, iodate, nitrate, nitrite, oxalate, oxide, perfluorophthalocyanine, peroxide, phosphate, phthalocyanine, pyrophosphate, silicate, sulphamate, sulphate, sulphide, sulphite, tartrate, tetrafluoroborate, thiocyanate, thiolate, thiosulphate, tosylate, and triflate.

6. The dye system of claim 3, wherein said at least one compound is selected from the group consisting of $TiBr_2$, $TiBr_4$, $TiCl_2$, $TiCl_3$, $TiCl_4$, $TiF_3$, $TiF_4$, $Ti_2O_3$, $TiO(SO_4)$, $(TiO_2)(SiO_2)$, $TiS_2$, $VBr_3$, $VCl_2$, $VCl_3$, $VCl_4$, $V_2O_3$, $V_2O_4$, $V_2O_5$, $VO(SO_4)$, $VOCl_3$, $VOF_3$, $V(C_5H_7O_2)_3$, $VO(C_5H_7O_2)_2$, $VO(OR)_3$, $Mo_2(OCOCH_3)_4$, $Mo(CO)_6$, $MoCl_3$, $MoCl_5$, $MoO_2Cl_2$, $MoF_6$, $MoO_2$, $MoO_3$, $MoS_2$, $MoOCl_4$, $MoSO_4$, $Mn(OCOCH_3)_2$, $Mn(OCOCH_3)_2.xH_2O$, $Mn(C_5H_7O_2)_2$, $MnBr_2$, $MnBr_2.xH_2O$, $MnCO_3$, $MnCO_3.xH_2O$, $Mn_2(CO)_{10}$, $MnCl_2$, $MnCl_2.xH_2O$, $MnF_2$, $MnF_3$, $Mn(HCO_2)_2.xH_2O$, $MnI_2$, $Mn(NO_3)_2$, $Mn(NO_3)_2.xH_2O$, $Mn_3O_4$, $Mn_2O_3$, $MnO_2$, $Mn(C_{32}H_{16}N_8)$, $MnSO_4$, $MnSO_4.xH_2O$, $MnS$, $Fe(OCOCH_3)_2$, $Fe(OCOCH_3)_3$, $FeBr_2$, $FeBr_3$, $FeCl_2$, $FeCl_2.xH_2O$, $FeCl_3$, $FeCl_3.xH_2O$, $Fe(OEt)_3$, $FeSO_4.NH_3CH_2CH_2NH_3SO_4.4H_2O$, $Fe_4[Fe(CN)_6]_3$, $FeF_2$, $FeF_3$, $FeF_3.xH_2O$, $FeI_2$, $Fe(CH_3CHOHCOO)_2.xH_2O$, $Fe(NO_3)_3.xH_2O$, $Fe(C_2O_4).xH_2O$, $FeO$, $Fe_2O_3$, $Fe_3O_4$, $FePO_4.xH_2O$, $Fe(C_{32}H_{16}N_8)$, $FeSO_4.xH_2O$, $FeS$, $Fe(BF_4)_4.xH_2O$, $FeO_3Ti$, $Fe(SCN)_2$, $Co(OCOCH_3)_2$, $Co(OCOCH_3)_2.xH_2O$, $Co(C_5H_7O_2)_2$, $Co(C_5H_7O_2)_2.xH_2O$, $Al_2CoO_4$, $CoBr_2$, $CoBr_2.xH_2O$, $CoCO_3$, $CoCO_3.xH_2O$, $CO_2(CO)_8$, $CoCl_2$, $CoCl_2.xH_2O$, $CoF_2$, $Co[CH_3(CH_2)_3CH(C_2H_5)CO_2]_2$, $Co(OH)_2$, $CoI_2$, $Co(NO_3)_2$, $Co(NO_3)_2.xH_2O$, $Co(C_2O_4)$, $Co(C_2O_4).xH_2O$, $CoSO_4$, $CoSO_4.xH_2O$, $Co(BF_4)_2$, $Co(BF_4)_2.xH_2O$, $Co(SCN)_2$, $Ni(OCOCH_3)_2$, $Ni(OCOCH_3).xH_2O$, $Ni(C_5H_7O_2)_2$, $NiBr_2$, $NiBr_2.xH_2O$, $NiCO_3$, $Ni(CO_3).xNi(OH)_2$, $NiCl_2$, $NiCl_2.xH_2O$, $NiOCoO$, $Ni[CH_3(CH_2)_3CH(C_2H_5)CO_2]_2$, $NiF_2$, $Ni(OH)_2$, $NiI_2$, $Ni(NO_3)_2$, $Ni(NO_3)_2.xH_2O$, $Ni(C_2O_4)$, $Ni(C_2O_4).xH_2O$, $NiO_2$, $NiO_2.xH_2O$, $Ni(C_{32}H_{16}N_8)$, $Ni(SO_3NH_2)_2$, $Ni(SO_3NH_2)_2.xH_2O$, $NiSO_4$, $NiSO_4.xH_2O$, $Ni_3S_2$, $NiZnFe_4O_4$, $CuOCOCH_3$, $Cu(OCOCH_3)_2$, $Cu(OCOCH_3)_2.xH_2O$, $Cu(C_5H_7O_2)_2$, $CuBr$, $CuBr_2$, $CuCO_3$, $CuCO_3.Cu(OH)_2$, $CuCl$, $CuCl_2$, $CuCl_2.xH_2O$, $Cu[CH_3(CH_2)_3CH(C_2H_5)CO_2]_2$, $CuF_2$, $CuF_2.xH_2O$, $Cu(HCO_2)_2$, $Cu(HCO_2)_2.xH_2O$, $Cu(OH)_2$, $Cu_2(OH)PO_4$, $CuI$, $CuFe_2O_4$, $Cu(NO_3)_2$, $Cu(NO_3)_2.xH_2O$, $Cu_2O$, $CuO$, $Cu(C_{32}H_{16}N_8)$, $Cu_2P_2O_7.xH_2O$, $CuSO_4$, $CuSO_4.xH_2O$, $CuS$, $Cu[O_2CCH(OH)CH(OH)CO_2].xH_2O$, $Cu(BF_4)_2$, $Cu(BF_4).xH_2O$, $Cu(SCN)$, $Zn(OCOCH_3)_2$, $Zn(OCOCH_3)_2.xH_2O$, $Zn(C_5H_7O_2)_2$, $Zn(C_5H_7O_2)_2.xH_2O$, $ZnBr_2$, $ZnBr_2.xH_2O$, $ZnCl_2$, $ZnF_2$, $Zn(C_{32}F_{16}N_8)$, $Zn(C_5HF_6O_2)_2$, $Zn(C_5HF_6O_2)_2.xH_2O$, $ZnSiF_6.xH_2O$, $ZnI_2$, $ZnFe_2O_4$, $Zn(NO_3)_2$, $Zn(NO_3)_2.xH_2O$, $Zn(C_2O_4)$, $Zn(C_2O_4).xH_2O$, $ZnO$, $ZnO.xH_2O$, $ZnO_2$, $Zn_3(PO_4)_2$, $Zn(C_{32}H_{16}N_8)$, $ZnSO_4$, $ZnSO_4.xH_2O$, $ZnS$, $Zn(BF_4)_2$, $Zn(BF_4)_2.xH_2O$, $Zn_2TiO_4$, $Zr(OCOCH_3)_4$, $Zr(OCOCH_3)_x(OH)_{4-x}$, $Zr(C_5H_7O_2)_4$, $Zr(C_{26}H_{44}O_{16})$, $ZrCO_3(OH_2)_2.ZrO_2$, $ZrCl_4$, $ZrF_4$, $ZrF_4.xH_2O$, $Zr(HPO_4)_2$, $Zr(OH)_4$, $ZrI_4$, $ZrO(NO_3)_2$, $ZrO(NO_3)_2.xH_2O$, $Zr(SO_4)_2$, $Zr(SO_4)_2.xH_2O$, $ZrOCl_2$, $ZrOCl_2.xH_2O$, $KAl(SO_4)_2$, $K_2CO_3$, $K_3PO_4$, $KNO_3$, $KCl$, $MgSO_4$, $Mg_3(PO_4)_2$, $MgCO_3$, $Mg(NO_3)_2$ and $MgCl_2$.

7. The dye system of claim 3, wherein said at least one metal-containing compound for use as a catalyst comprises at least one metal complex comprising an organic ligand.

8. The dye system of claim 1, wherein said at least one dye precursor is an organic precursor, which optionally comprises at least one aromatic amino compound, phenolic compound, or aminophenolic compound and is optionally selected from the group consisting of p-aminophenol (4), o-aminophenol (5), p-amino-o-cresol (8), m-aminophenol (9), p-chlororesorcinol (10), 2,3-dihydroxynaphthalene (11), 3-methylcatechol (12), 4-methylresorcinol (14), p-aminobenzoic acid (15), 1,3-dihydroxynaphthalene (16) and 1,4-dihydroxynaphthalene (17), or comprises at least one naturally occurring compound or derivative thereof:

9. The dye system of claim 8, wherein said at least one naturally occurring compound or derivative thereof comprises at least one phenolic compound or derivative thereof and said at least one naturally occurring phenolic compound or derivative thereof is selected from the group consisting of gallic acid (18), tannic acid (19), vanillin (20), phloroglucinol (21), orcinol (22) and 5-aminosalicylic acid (23):

10. The dye system of claim 8, wherein said at least one organic precursor comprises isatin (24), 1-methylindole (25) or 2-methylindole (26), or said at least one aromatic amino compound comprises N,N-bis(hydroxyethyl)-p-phenylenediamine (27):

-continued

25

26

27

11. The dye system of claim 1, wherein said oxidising agent is selected from the group consisting of percarbonates, persulphates, organic peracids, organic hydroperoxides, molecular oxygen and air, or is hydrogen peroxide.

12. A method for the coloration of a substrate, said method comprising:
(a) treating said substrate with at least one dye precursor;
(b) treating said substrate with an oxidising agent; and
(c) treating said substrate with a catalyst,
wherein said catalyst is a homogeneous catalyst or a heterogeneous catalyst and said method is optionally performed by treating said substrate in aqueous solutions comprising said dye precursor, oxidising agent and catalyst;
further wherein said substrate comprises a natural or synthetic polymeric substrate, which is optionally selected from polyethylene, polyvinyl chloride, rubber or leather, and a textile fiber substrate, which optionally comprises at least one of cotton, wool, polypropylene, polyester, polyetherketone, p-aramid, m-aramid or lyocell;
and which is carried out at pressures of 1-500 bar, optionally at atmospheric pressure and at a temperature in the range from 20°-110° C., or at pressures of 1-20 bar and elevated temperatures in the range from 100°-200° C.

13. The method of claim 12 which is carried out at ambient temperatures.

14. A method for the coloration of a substrate, said method comprising:
(a) treating said substrate with at least one dye precursor;
(b) treating said substrate with an oxidising agent; and
(c) treating said substrate with a catalyst,
wherein said catalyst is a homogeneous catalyst or a heterogeneous catalyst and said method is optionally performed by treating said substrate in aqueous solutions comprising said dye precursor, oxidising agent and catalyst;
and further wherein said substrate comprises a textile fiber substrate which comprises wool and said method is carried out at a pH in the range of 5-8.

15. The method of claim 12, wherein said catalyst comprises at least one metal-containing compound, wherein said at least one metal-containing compound optionally comprises at least one inorganic metal compound, which optionally comprises at least one metal complex comprising an organic ligand.

16. The method of claim 12, wherein said at least one dye precursor comprises an organic precursor, which optionally comprises at least one aromatic amino compound, phenolic compound or aminophenolic compound.

17. The method of claim 12, wherein said oxidising agent is selected from the group consisting of percarbonates, persulphates, organic peracids, organic hydroperoxides, molecular oxygen, air, and hydrogen peroxide.

18. The method of claim 13 which is carried out at ambient temperatures.

* * * * *